(12) United States Patent
Wieters et al.

(10) Patent No.: US 10,056,179 B2
(45) Date of Patent: Aug. 21, 2018

(54) ELECTROMAGNETIC ACTUATOR FOR A SURGICAL INSTRUMENT AND METHOD FOR SETTING A STROKE DISTANCE

(71) Applicant: OLYMPUS WINTER & IBE GMBH, Hamburg (DE)

(72) Inventors: Martin Wieters, Hamburg (DE); Andreas Noack, Drage (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 341 days.

(21) Appl. No.: 14/742,830

(22) Filed: Jun. 18, 2015

(65) Prior Publication Data
US 2015/0287508 A1 Oct. 8, 2015

Related U.S. Application Data

(63) Continuation of application No. PCT/EP2013/003609, filed on Nov. 29, 2013.

(30) Foreign Application Priority Data

Dec. 21, 2012 (DE) ........................ 10 2012 224 177

(51) Int. Cl.
*H01F 41/00* (2006.01)
*H01F 7/08* (2006.01)
(Continued)

(52) U.S. Cl.
CPC ......... *H01F 7/081* (2013.01); *A61B 1/00183* (2013.01); *A61B 1/00188* (2013.01);
(Continued)

(58) Field of Classification Search
CPC ..... H01F 7/1607; H01F 7/1615; H02K 33/00; A61B 17/00; A61B 1/011; A61B 2017/00398; G02B 7/102; G02B 23/2407
(Continued)

(56) References Cited

U.S. PATENT DOCUMENTS 3,902,085 A * 8/1975 Bizzigotti .............. H02N 2/023
 310/25
4,882,511 A * 11/1989 von der Heide ....... G11B 19/20
 310/67 R
(Continued)

FOREIGN PATENT DOCUMENTS

DE 69403613 T2 1/1998
DE 202009002433 U1 6/2009
(Continued)

OTHER PUBLICATIONS

English translation of a Chinese Office Action dated Jul. 19, 2016 in related Chinese Patent Application No. 201380066486.2.
(Continued)

*Primary Examiner* — Forrest M Phillips
(74) *Attorney, Agent, or Firm* — Scully, Scott, Murphy & Presser, P.C.

(57) ABSTRACT

An electromagnetic actuator for a medical instrument including: a stator; and a movable element, at least partly composed of a paramagnetic and/or a ferromagnetic material, and which can be reversibly moved from a first to a second position by the application of a switchable magnetic field, wherein the stator and the movable element have annular distal and proximal pole shoes corresponding to each other, wherein the distal pole shoes and/or the proximal pole shoes of the stator and the movable element are aligned with each other in an overlapping manner in the first and/or the second position, and the distal pole shoes and/or the proximal pole shoes of the stator and the movable element have a structure in the circumferential direction on the surfaces of pole shoes facing each other, with the structures corresponding to each other.

20 Claims, 2 Drawing Sheets

(51) Int. Cl.
*A61B 1/00* (2006.01)
*G02B 7/10* (2006.01)
*G02B 23/24* (2006.01)
*H01F 7/16* (2006.01)
*H02K 33/00* (2006.01)
*H01F 7/122* (2006.01)
*A61B 17/00* (2006.01)

(52) U.S. Cl.
CPC .............. *A61B 17/00* (2013.01); *G02B 7/102* (2013.01); *G02B 23/2407* (2013.01); *H01F 7/122* (2013.01); *H01F 7/1607* (2013.01); *H01F 7/1615* (2013.01); *H02K 33/00* (2013.01); *A61B 1/0011* (2013.01); *A61B 2017/00398* (2013.01); *A61B 2017/00876* (2013.01)

(58) Field of Classification Search
USPC .......................................................... 310/25
See application file for complete search history.

(56) References Cited

U.S. PATENT DOCUMENTS

| | | | | |
|---|---|---|---|---|
| 5,215,449 A * | 6/1993 | Ilija | ..................... | F02M 39/005 417/304 |
| 5,627,418 A | 5/1997 | Satomi | | |
| 6,346,107 B1 * | 2/2002 | Cucin | .............. | A61B 17/32002 604/35 |
| 8,206,408 B2 | 6/2012 | Rebstock et al. | | |
| 8,922,067 B2 | 12/2014 | Vogel | | |
| 2007/0010707 A1 | 1/2007 | Leiner et al. | | |
| 2011/0308888 A1 * | 12/2011 | Carothers | ............... | F16N 13/04 184/6.1 |
| 2013/0193778 A1 * | 8/2013 | Wieters | .............. | A61B 1/00133 310/12.04 |
| 2014/0246478 A1 * | 9/2014 | Baber | .................. | A61B 17/068 227/180.1 |
| 2015/0223674 A1 * | 8/2015 | Wieters | .............. | A61B 1/00096 74/89 |
| 2015/0280537 A1 * | 10/2015 | Nishiura | ............ | A61C 17/3445 15/22.2 |
| 2015/0380144 A1 * | 12/2015 | Heravi | .................. | F16D 48/064 361/139 |
| 2016/0029562 A1 * | 2/2016 | De Smet | ................. | A01F 12/32 460/1 |

FOREIGN PATENT DOCUMENTS

| | | |
|---|---|---|
| DE | 102011006814 A1 | 1/2012 |
| DE | 102011005255 A1 | 9/2012 |
| EP | 2362529 A2 | 8/2011 |

OTHER PUBLICATIONS

International Search Report dated Mar. 20, 2014 issued in PCT/EP2013/003609.

* cited by examiner

ELECTROMAGNETIC ACTUATOR FOR A SURGICAL INSTRUMENT AND METHOD FOR SETTING A STROKE DISTANCE

CROSS-REFERENCE TO RELATED APPLICATION

The present application is a continuation of PCT/EP2013/003609 filed on Nov. 29, 2013, which is based upon and claims the benefit to DE 10 2012 224 177.9 filed on Dec. 21, 2012, the entire contents of each of which are incorporated herein by reference.

BACKGROUND

Field

The present application relates to an electromagnetic actuator for a surgical or medical instrument, wherein the actuator comprises a stator and a movable element, which is at least partly composed of a paramagnetic and/or ferromagnetic material and which can be reversibly moved from a first position to a second position by the application of a switchable magnetic field, wherein the stator and the movable element have annular distal and proximal pole shoes that correspond to each other, wherein the distal pole shoes and/or the proximal pole shoes of the stator and the movable element are aligned with each other in an overlapping manner in the first position and/or in the second position. The application further relates to a surgical or medical instrument having a corresponding actuator.

Prior Art

From the document DE 10 2011 006 814 A1, an electromagnetic actuator for a surgical or medical instrument is known, wherein the actuator has a stator and a movable element, which is at least partially comprised of a paramagnetic or ferromagnetic material and can be moved from a first position into a second position by applying an electromagnetic field. Here, the movable element is held in the first or the second position by a permanent magnetic field.

The concept disclosed in document DE 10 2011 006 814 A1 for an electromagnetic actuator is used in order to move an optical component axially to the optical axis, wherein the optical component is located in the traveller. Thus, it is possible to change, for example, a focus or an enlargement of the optical system, or to change a viewing direction.

Due to repeated translatory movement or external influences such as vibrations or assembly forces, it is possible that the optical system is no longer in optimal focus. This can occur after the installation or after multiple actuations of the actuator, for instance due to manufacturing defects in the components or also positioning and alignment errors during the assembly, wherein a rotational movement of the traveller can occur. These errors are compensated by compensation procedures such as focusing and meniscus placement during the assembly, however the optical system is optimized only in one state. If subsequent changes to the optical system occur, this can negatively influence the reproduced image quality.

A further effect is that with a bistable actuator, the stroke of the actuator is set between two surfaces oriented orthogonally to the optical axis, for example stop surfaces or traveller surfaces, and these can deviate from their orthogonality to the optical axis due to manufacturing and assembly inaccuracies. This can lead to the fact that the actual stroke can be larger or smaller than intended due to the deviations, and in the case of a freely rotatable traveller can even vary.

Still further with such actuators, the setting of the stroke distance with the assembly is very complex.

SUMMARY

In contrast, an object is, with an electromagnetic actuator for a surgical or medical instrument (hereinafter collectively referred to as a medical instrument), to compensate errors of the optical system with minimal constructive effort, and further to simplify the setting of the stroke distance.

This object is solved by an electromagnetic actuator for medical instrument, wherein the actuator comprises a stator and a movable element, which is at least partly composed of a paramagnetic and/or ferromagnetic material, and which can be reversibly moved from a first position to a second position by the application of a switchable magnetic field, wherein the stator and the movable element have annular distal and proximal pole shoes that correspond to each other, wherein in the first position and/or in the second position the distal pole shoes and/or the proximal pole shoes of the stator and the movable element are aligned with each other in an overlapping manner, which is further developed in that the distal pole shoes and/or the proximal pole shoes of both the stator and the movable element have structures in the circumferential direction on the surfaces of the pole shoes facing each other, with the structures corresponding to each other.

The structures corresponding to each other on the surfaces facing each other lead to the fact that the stator and the movable element, or respectively the traveller of the actuator, are held in a fixed angular relationship to each other. The magnetic flux lines seek the path of least resistance, which leads to the fact that the protruding, thus, projecting regions of the structured surfaces of the pole shoes are aligned to each other as precisely as possible. Hereby, the gap between the pole shoes is minimized at the locations of the projecting regions, whereby a state of lower energy is assumed.

The inventive principle of the structured pole shoes can be used advantageously in different types of electromagnetic actuators, for example with bistable reluctance actuators or with Lorentz force actuators.

Alignment in an overlapping manner, or aligned overlapping is understood to mean that in the first and/or the second position, the surfaces of the structures facing each other, or respectively the pole shoe segments of the pole shoes facing each other, are overlapping at least partially. The overlapping does not need to be complete, because the corresponding permanent magnetic field should exert an axial force also at the stop at this position which holds the movable element in the corresponding position. Therefore, in the scope of the invention, a partial overlapping is sufficient if the function of the force transfer in the circumferential direction is guaranteed by the bundling of the magnetic field lines due to the structures of the pole shoes.

Both the proximal as well as the distal pole shoes can each at least partially overlap in both positions. Thus, the rotational coupling of the traveller to the stator can occur over the entire length of the stator, such that torsions of the traveller with respect to the stator are avoided.

The disadvantages of the prior art are overcome in that the angular relationship of the stator and traveller, or respectively the movable element, are fixed to each other by means of the structured surfaces of the pole shoes. Now, a loss of adjustment can no longer occur since the traveller, or respectively the movable element, rotates in the stator due to multiple switching, and thus leading to a deviation from the optimized arrangement with the assembly. Thus, the rotational position to the remainder of the optical system is maintained. Because the traveller, or respectively the movable element, is held in a defined rotational position to the stator, the image quality is no longer changed despite actuations of the actuator. Furthermore, the rotational position of the movable element is now fixed such that the same stroke distance remains reproducible irrespective of assembly inaccuracies or manufacturing inaccuracies in the installation of the stop surfaces.

Thus, it is not necessary to use a mechanical guide for the rotational position, which is complex depending on construction and is associated with an additional increase of the friction in the system.

The structures of the surfaces of the pole shoes corresponding to each other can comprise pole shoe segments. These pole shoe segments represent sections of the pole shoes which are widened outward, or respectively inward, with respect to the remainder of the pole shoe, such that the gap between the pole shoe segments facing each other is smaller than between the parts of the pole shoes without pole shoe segments. Due to these radial structures, the magnetic flux is directed such that one or more rotational positions result in which the magnetic resistance of the magnetic circuit is less than in the other rotational positions. If the movable element, or respectively the traveller, is rotated out of the position with the lowest magnetic resistance, a torque arises that is directed against the rotation, because the magnetic system seeks to attain the state of the lowest energy, or respectively the least magnetic resistance.

In one design, the two pole shoes of the stator and the two pole shoes of the movable element are formed identically and/or are arranged in the same angular relationship to each other, such as having a rotationally symmetrical shape, such as a 3-fold or higher number rotational symmetry. Of particular stability here are, for example, odd numbered rotational symmetries, such as 3-fold, 5-fold or 7-fold, however, even numbered rotational symmetries such as 6-fold or 8-fold can also be used.

Alternatively, the two poles of the stator and the two pole shoes of the movable element can be formed differently from each other, and can have different numbers of pole shoe segments and/or are arranged in different angular relationships to each other. Thus for example, the distal pole shoe can have a 3-fold rotational symmetry and the proximal pole shoe can have a 5-fold rotational symmetry, wherein the pole shoes of the stator are designed correspondingly, or in each case the same rotational symmetry can be selected, wherein however the individual pole shoe segments of the distal and the proximal pole shoe need not align with each other such that they have a different angular relationship to each other. In this manner, the return force in the circumferential direction can be set uniformly.

The movable element can or will be held in the first position by a permanent magnetic field, and after moving into the second position, can or will be held in the second position by a permanent magnetic field. This embodiment represents a bistable actuator.

Two stops are can be provided which define the first and the second position, wherein in particular, with the movable element resting against a stop, a force is exerted on the movable element in the direction of the stops. The force exerted on the movable element in the direction of the stops is generated by the permanent magnetic field at the corresponding position, so that the stops limit the movement of the movable element such that they cannot enter into a configuration with minimal energy. In the minimal magnetic and energetic configuration, force would no longer be exerted on the movable element, and its position would not be defined, or respectively, could be moved easily.

In a further aspect, the setting of the stroke distance of the electromagnetic actuator is advantageously attainable in that at least one stop has a connecting member, aligned toward the movable element, the height of the connecting member being modulated in the circumferential direction, wherein the movable element on one side, which in the first or second position rests against the stop with the connecting member, has contact elements, which rest on the connecting member such that the axial position at the stop can be set with a rotation of the movable element about its central axis. Using the connecting member it is possible to determine, using a rotation of the movable element according to the invention, at which position the movable element actually contacts the stop with the connecting member, so that in this manner the stroke distance, or respectively, the stop point, in the axial direction is determined.

For this purpose, the connecting member has a triple or higher multiple sawtooth shape, wherein the connecting member is formed, such as perpendicular to the central axis of the actuator in the radial direction, as a circle, as a closed curve with radial variation or as a series of spiral segments. With a triple or higher multiple sawtooth shape, three or more contact points are present for the movable element at the stop, or respectively at the connecting member, such that a stable resting on the stop is guaranteed. A connecting member, which is triangular in the top view, can also be used. The individual sections of the connecting member could be, but do not have to be, connected together.

The stator can comprise two permanent magnets, which are poled to repel each other, such as in the axial direction. This configuration allows a stable stop location in both positions. A coil for generating the switchable magnetic fields can be provided, such as arranged in between the permanent magnets.

A particularly simple embodiment is attained when the movable element is mounted longitudinally axially movable in a tube, wherein the movable element, the coil for generating the switchable magnetic field and/or the permanent magnets can be annular in section. The pole shoes can be composed at least to some extent from a ferromagnetic material.

The object can also be solved by a medical instrument, such as an endoscope, having the aforementioned actuator, wherein the stator of the electromagnetic actuator can be arranged in a part that can be rotated in the circumferential direction with respect to a handle of the instrument. In this manner, the instrument obtains a reproducible quality of the optics, even in the event of multiple actuations of the actuator, and, if applicable, a settable stroke distance. Here, the stator can be rotated by hand, or in another manner, such that due to the rotation of the stator, the traveller, or respectively the movable element, can be moved along with it, and thus, stop positions or stroke distance can be set.

Finally, the object can also be solved by a method for setting the stroke distance of an electromagnetic actuator of an aforementioned medical instrument, wherein the movable element of the actuator can or will be brought into the position in which it rests against the connecting member of the stop that is provided with a connecting member, and the stator of the electromagnetic actuator is rotated in the circumferential direction, whereby the movable element is rotated in the circumferential direction via the pole shoes, structured in the circumferential direction, and the movable element is set in its axial position via the connecting member.

The characteristics, advantages and properties of the subject matters of the application, thus, the device, the instrument and the method apply without restriction also to the respective other subject matters, which relate to each other.

Further characteristics will become apparent from the description of the embodiments together with the claims and the included drawings. Embodiments can fulfill individual characteristics or a combination of several characteristics.

BRIEF DESCRIPTION OF THE DRAWINGS

The embodiments are described below, without restricting the general idea of the invention, using exemplary embodiments with reference to the drawings, whereby we expressly refer to the drawings with regard to the disclosure of all details according to the invention that are not explained in greater detail in the text. In the figures.

DETAILED DESCRIPTION

Figure 1:
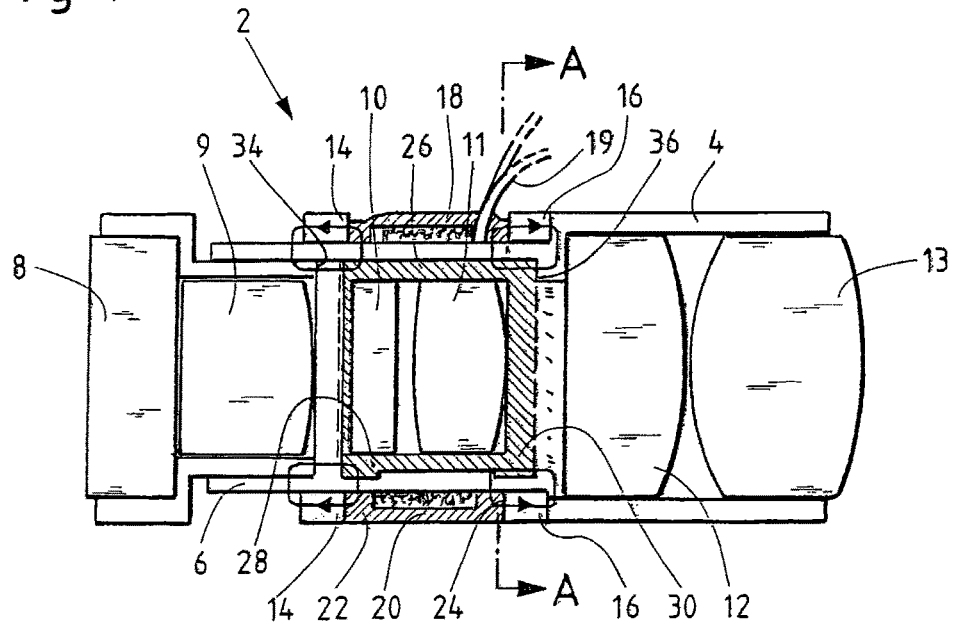
FIG. 1 illustrates a schematic longitudinal sectional view through an actuator.

In the drawings, the same or similar elements and/or parts are provided with the same reference numbers in order to prevent the item from needing to be reintroduced.

In FIG. 1, a sliding tube 4, in which lenses 12, 13 are arranged in a lens arrangement, can be seen in a schematic longitudinal section through an actuator 2. A lens holder 6 is arranged distally in the inner sliding tube 4 for distal input lenses 8, 9 of the lens arrangement, wherein the lens holder 6 is securely connected to the sliding tube 4.

Between the lenses 8, 9 and 12, 13 two further lenses 10, 11 of the lens arrangement are represented that are enclosed in an enclosure made of soft magnetic material, which has in each case, at its proximal and distal end, a distal pole shoe 28, or respectively a proximal pole shoe 30. This enclosure forms the traveller of the actuator 2. As seen in the lower region of FIG. 1, the pole shoes 28, 30 are structured in the radial direction along the circumference.

An arrangement comprised of two permanent magnets 14, 16 forms the stator of the actuator 2, between which a coil 18, having connection lines 19, is arranged for generating a switchable magnetic field, wherein a cover 20 is provided composed of a soft magnetic material, which partially encloses the coil 18. The cover 20 is also structured radially in the circumferential direction having an odd numbered rotational symmetry, which is visible by the asymmetry of the upper and the lower sectional representation to one another. The sliding tube 4 is arranged in the gap between the movable element 26 and the stator. The respectively closed magnetic field lines are also shown schematically in FIG. 1.

A part of the sliding tube 4 and the end of the lens holder 6 form stops 34, 36 for the movable element 26 and determine the stroke distance of the electromagnetic actuator 2.

In the first position, in which the movable element 26 rests against the first stop 34, thus distally, the surface of the distal pole shoe 28 aligns at least overlapping with the pole shoe 22 of the outer stator. In the second position against the stop 36, the proximal pole shoes 24, 30 align overlapping each other. In both positions, the respectively other pole shoes can still partially overlap each other such that the radial structure in the circumferential direction produces an effect both distally and also proximally.

Figure 2:
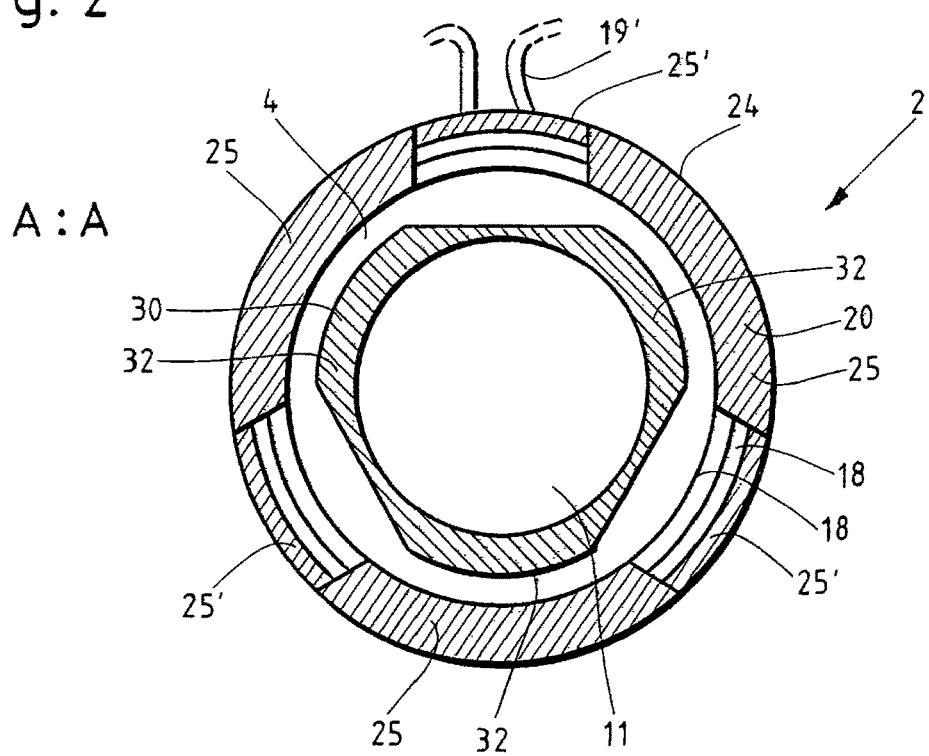
FIG. 2 illustrates a schematic cross-sectional representation through the actuator according to FIG. 1.

FIG. 2 shows a schematic cross-sectional representation along the cutting line A-A from FIG. 1, wherein proceeding from inward toward outward, the lens 11 is shown most inward, enclosed by soft magnetic proximal pole shoe 30, which has a three-fold symmetry with three pole shoe segments 32. The pole shoe segments 32 are implemented thicker in comparison to the remainder of the pole shoe 30, and narrow the gap outward. The sliding tube 4 lies between the proximal pole shoe 30 and the proximal pole shoe 24 of the outer stator. This stator is also structured in the circumferential direction and has on one side pole shoe segments 25 and on the other side openings 25', wherein the magnetic field lines enter, in particular through the soft magnetic material of the pole shoe at the pole shoe segments 25, into the pole shoe segments 32 of the traveller. Furthermore, the coil 18 having multiple windings can be seen in the openings 25'.

The arrangement, in each case, of the three pole shoe segments 32, 25 facing each other ensures that these are guided in a fixed angular relationship to each other without any mechanical guide structures required for this purpose.

Figure 3:
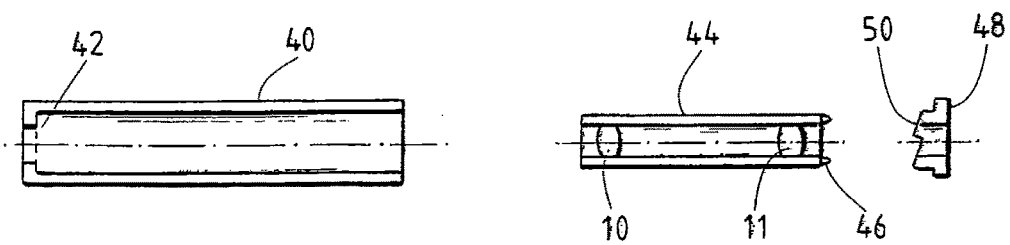
FIG. 3 illustrates a schematic representation of a further design of an actuator.

FIG. 3 shows a simple example of a further electromagnetic actuator in a few mechanical aspects. This actuator has a sliding tube 40 having a first stop 42, into which a traveller tube 44, having two lenses 10, 11 of the lens system, is inserted. The traveller tube 44 has proximally a plurality of stop pins 46. After insertion of the traveller tube 44 into the sliding tube 40, the sliding tube 40 is sealed with a stop sleeve 48 having a controlled gate or connecting member 50. The further magnetic and electromagnetic components are not shown in FIG. 3.

In the second position, thus the proximal position, the stop pins 46 of the traveller tube 44 rest on the connecting member 50. A rotation of the traveller tube 44 using the transfer via the structured pole shoes according to FIGS. 1 and 2, results in that the stop pins 46 of the traveller tube 44, depending on rotational positioning, rest on another location of the connecting member 50 such that the axial position can be defined by a rotation of the traveller tube 44 about its central axis.

The connecting member 50 can be shaped as a ring, which has the same diameter as the stop pins 46 of the traveller tube 44, wherein this ring is height modulated in the axial direction, for example having three or more sawtooth modulations.

Instead of the stop pins 46, radially directed stop ridges or stop lines can be provided which interact with a connecting member 50, which is not necessarily shaped circularly, or can for example also have a plurality of spiral section shaped elevations that are not connected together.

Figure 4:
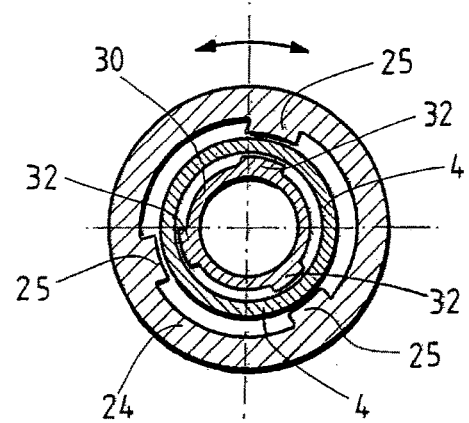
FIG. 4 illustrates a schematic cross-sectional representation through the actuator according to FIG. 3.

FIG. 4, in turn, shows a cross-section perpendicular to the central axis of the actuator, wherein one embodiment is shown in which a proximal pole shoe having discrete pole shoe segments 32, being raised in comparison to the otherwise annular pole shoe 30, is arranged in the interior of the sliding tube 4. Shown outside of the traveller tube 4, the pole shoe 24 of the outer stator is also substantially annular in cross-section and has inward pointing pole shoe segments 25, the width of which corresponds to the width of the pole shoe segments 32 of the pole shoe 30 of the traveller, thus of the movable element 26. In this manner, a well-defined guidance of the magnetic circuits in the pole shoes in the circumferential direction is attained and, with movement of the pole shoe 24, a strong force to carry along in the direction of the arrow.

All named features, including those to be taken from the drawings alone, and individual features which are disclosed in combination with other features, are considered individually and in combination as being important to the invention. Embodiments according to the invention can be fulfilled through individual characteristics or a combination of several characteristics.

LIST OF REFERENCE SYMBOLS 2 electromagnetic actuator
4 sliding tube
6 lens holder
8-13 lens
14 permanent magnet
16 permanent magnet
18 coil
19 connection line
20 cover
22 distal pole shoe
24 proximal pole shoe
25 pole shoe segment
25 opening
26 movable element
28 distal pole shoe
30 proximal pole shoe
32 pole shoe segment
34 first stop
36 second stop
40 sliding tube
42 first stop
44 traveller tube
46 stop pins
48 stop sleeve
50 contoured connecting member

What is claimed is:

1. An electromagnetic actuator for a medical instrument, wherein the actuator comprises:
  a stator; and
  a movable element, which is at least partly composed of one or both of a paramagnetic and a ferromagnetic material, and which can be reversibly moved in a longitudinal direction from a first position to a second position by the application of a switchable magnetic field,
  wherein the stator and the movable element have annular distal and proximal pole shoes that correspond to each other, wherein one or both of the distal pole shoes and the proximal pole shoes of the stator and the movable element are aligned with each other in an overlapping manner in one or both of the first position and the second position, and
  at least one of the distal pole shoes of the stator and the movable element and the proximal pole shoes of the stator and the movable element extend in the radial direction such that surfaces of the at least one of the distal pole shoes of the stator and the movable element and the proximal pole shoes of the stator and the movable element face each other along the longitudinal direction.

2. The electromagnetic actuator according to claim 1, wherein the structures of the surfaces of the pole shoes corresponding to each other comprise pole shoe segments.

3. The electromagnetic actuator according to claim 1, wherein the two pole shoes of the stator and the two pole shoes of the movable element are formed one or more of identically to each other and are arranged in the same angular relationship to each other.

4. The electromagnetic actuator according to claim 1, wherein the two pole shoes of the stator and the two pole shoes of the movable element are formed differently from each other.

5. The electromagnetic actuator according to claim 1, wherein the movable element is held in the first position by a permanent magnetic field, and after moving into the second position, is held in the second position by a permanent magnetic field.

6. The electromagnetic actuator according to claim 1, further comprising two stops which define the first and the second position, respectively, wherein with contact of the movable element on one of the two stops, a force acts on the movable element in the direction of the stops.

7. The electromagnetic actuator according to claim 6, wherein at least one of the two stops has a connecting member directed toward the movable element, the height of which is modulated in the circumferential direction, wherein the movable element at one side, which in the first or second position rests against the at least one of the two stops with the connecting member, has contact elements, which rest on the connecting member such that the axial position on the at least one of the two stops can be set by a rotation of the movable element about its central axis.

8. The electromagnetic actuator according to claim 7, wherein the connecting member has three or more sawtooths.

9. The electromagnetic actuator according to claim 8, wherein the connecting member is formed as one of a circle perpendicular to the central axis of the actuator in the radial direction, as a closed curve having radial variations, or as a series of spiral segments.

10. The electromagnetic actuator according to claim 1, wherein the stator comprises two permanent magnets poled to repel each other in the axial direction.

11. The electromagnetic actuator according to claim 1, further comprising a coil for generating the switchable magnetic field arranged between the permanent magnets.

12. The electromagnetic actuator according to claim 10, wherein the movable element is mounted longitudinally axially movable in a tube.

13. The electromagnetic actuator according to claim 12, wherein one or more of the movable element, the coil for generating the switchable magnetic field and the permanent magnets are annular in section.

14. The electromagnetic actuator according to claim 1, wherein the distal and proximal pole shoes are at least partially composed of a ferromagnetic material.

15. A medical instrument comprising the electromagnetic actuator according to claim 1.

16. The medical instrument according to claim 15, wherein the stator of the electromagnetic actuator is arranged in a part rotatable in the circumferential direction with respect to a handle of the instrument.

17. The electromagnetic actuator according to claim 3, wherein the two pole shoes of the stator and the two pole shoes of the movable element are formed in the same angular relationship to each other to have a rotationally symmetrical shape.

18. The electromagnetic actuator according to claim 17, wherein the rotationally symmetrical shape is a 3-fold or higher number rotational symmetry.

19. The electromagnetic actuator according to claim 4, wherein the two pole shoes of the stator and the two pole shoes of the movable element are formed having one or more of different numbers of pole shoe segments and are arranged in a different angular relationship to each other.

20. A method for setting a stroke distance of an electromagnetic actuator of a medical instrument, the method comprising:
- bringing the movable element of the actuator into a position in which it rests against a connecting member of a stop provided with a connecting member, and
- rotating a stator of the electromagnetic actuator in the circumferential direction, whereby the movable element is rotated in the circumferential direction via pole shoes having portions structured to extend in the circumferential direction from other surfaces of the pole shoes, and the axial position thereof is set via the connecting member.

\* \* \* \* \*